(12) United States Patent
Mizuo et al.

(10) Patent No.: US 6,232,324 B1
(45) Date of Patent: *May 15, 2001

(54) USE OF PYRAZOLOPYRIDINE COMPOUND

(75) Inventors: Hiroyuki Mizuo, Mino; Tokuaki Kajiho, Kobe; Haruo Horiai, Yokohama; Yukio Motoyama, Tsukuba; Kimio Esumi, Kobe, all of (JP)

(73) Assignee: Fujisawa Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 68 days.

(21) Appl. No.: 08/945,175

(22) PCT Filed: Apr. 18, 1996

(86) PCT No.: PCT/JP96/01063

§ 371 Date: Oct. 24, 1997

§ 102(e) Date: Oct. 24, 1997

(87) PCT Pub. No.: WO96/33715

PCT Pub. Date: Oct. 31, 1996

(30) Foreign Application Priority Data

Apr. 27, 1995 (JP) ............................................ 7-103588

(51) Int. Cl.$^7$ .................. A61K 31/437; A61K 31/4545; A61K 31/501

(52) U.S. Cl. .......................... 514/322; 514/253; 514/300; 514/254

(58) Field of Search .................................. 514/300, 253, 514/322, 254

(56) References Cited

FOREIGN PATENT DOCUMENTS 0 299 209 * 1/1989 (EP) .

* cited by examiner

*Primary Examiner*—Phyllis G. Spivack
(74) *Attorney, Agent, or Firm*—Oblon, Spivak, McClelland, Maier & Neustadt, Neustadt

(57) ABSTRACT

The present invention relates to a pharmaceutical composition for the prevention and/or the treatment of dialysis-induced hypotension and/or hypotension after dialysis which comprises, as an active ingredient, a pyrazolopyridine compound of the following formula (I)

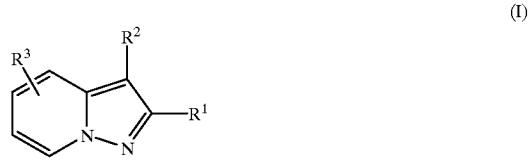

wherein the groups $R^1$, $R^2$ $R^3$, or a said thereof are herein defined.

22 Claims, No Drawings

USE OF PYRAZOLOPYRIDINE COMPOUND

This case is a 371 of PCT/JP96/01063 filed Apr. 18, 1996.

TECHNICAL FIELD

The present invention relates to a pharmaceutical composition for the prevention and/or the treatment of dialysis-induced hypotension and/or hypotension after dialysis which comprises, as an active ingredient, a pyrazolopyridine compound or a salt thereof, and so is useful in the pharmaceutical field. Here, hypotension after dialysis includes postural hypotension after dialysis.

BACKGROUND ART

Some pyrazolopyridine compounds are known to be useful as diuretic, antihypertensive agent, remedy for renal insufficiency, and the like (e.g. Japanese Laid-Open Nos. 64-45385, 2-243689, 5-112566, etc.).

DISCLOSURE OF INVENTION

A pharmaceutical composition for the prevention and/or the treatment of dialysis-induced hypotension and/or hypotension after dialysis of the present invention is the one which comprises, as an active ingredient, a pyrazolopyridine compound or a salt thereof.

The pyrazolopyridine compound to be used in the present invention is shown by the following formula (I):

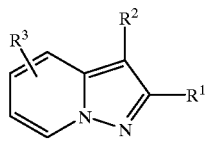

wherein
$R^1$ is lower alkyl, aryl which may have one or more suitable substituent(s) or a heterocyclic group,
$R^2$ is a group of the formula

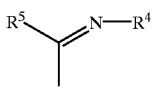

(wherein
$R^4$ is protected amino or hydroxy and
$R^5$ is hydrogen or lower alkyl); cyano;
a group of the formula:

(wherein
$R^6$ is an acyl group, and
A is lower aliphatic hydrocarbon group which may have one or more suitable substitutent(s));
amidated carboxy;
unsaturated heterocyclic group which may have one or more suitable substituent(s); amino or protected amino; and
$R^3$ is hydrogen, lower alkyl, lower alkoxy or halogen or a salt thereof.

As for aforesaid pyrazolopyridine compound (I), the known compounds disclosed in Japanese Laid-Open Nos. 64-45385, 2-243689, 4-253978 and 5-112566 are exemplified.

Further, in addition to aforesaid pyrazolopyridine compound (I), the pyrazolopyridine compound disclosed in WO95/18128 (in particular, the compounds of claims 5 and 8 such as 3-[2-(4-carboxy-2-oxocyclohexyl)-3-oxo-2,3-dihydropyridazin-6-yl]-2-phenylpyrazolo[1,5-a]pyridine, 3-[2-(2-carboxymethyl-1-cyclohexenyl)-3-oxo-2,3-dihydropyridazin-6-yl]-2-phenylpyrazolo[1,5-a]pyridine, or the like) can be also used, according to the present invention, as a pharmaceutical composition for the prevention and/or the treatment of dialysis-induced hypotension and/or hypotension after dialysis.

Suitable salts of the pyrazolopyridine compound (I) in the present invention are conventional ones and include a metal salt such as an alkali metal salt (e.g. sodium salt, potassium salt, etc) and an alkaline earth metal salt (e.g. calcium salt, magnesium salt, etc), an ammonium salt, an organic base salt (e.g. trimethylamine salt, triethylamine salt, pyridine salt, picoline salt, dicyclohexylamine salt, N,N'-dibenzylethylenediamine salt, etc), an organic acid salt (e.g. acetate, trifluoroacetate, maleate, tartrate, fumalate, methanesulfonate, benzenesulfonate, formate, toluenesulfonate, etc), an inorganic acid salt (e.g. hydrochloride, hydrobromide, hydriodide, sulfate, phosphate, etc), a salt with an amino acid (e.g. arginine, aspartic acid, glutamic acid, etc), and the like.

In the above and following descriptions of the present specification, suitable examples and illustrations of the various definitions which the present invention includes within the scope thereof are explained in detail as follows.

The term "lower" is intended to mean 1 to 6 carbon atom(s) unless otherwise indicated.

The term "higher" is intended to mean 7 to 20 carbon atoms unless otherwise indicated.

Suitable "lower aliphatic hydrocarbon group" may include lower alkyl, lower alkenyl, lower alkynyl as explained below and the like.

Suitable "lower alkyl" may include straight or branched ones such as methyl, ethyl, propyl, isopropyl, butyl, t-butyl, pentyl, hexyl or the like, in which the preferred one may be $(C_1-C_4)$alkyl and the more preferred one may be methyl, ethyl, propyl and isopropyl.

Suitable "lower alkenyl" may include straight or branched ones such as vinyl, 1-methylvinyl, 2-methylvinyl, 1-propenyl, 2-propenyl, 1-butenyl, 2-methyl-1-propenyl, 1,3-butadienyl, 1-pentenyl, 4-pentenyl, 1-hexenyl, 1,4-hexadienyl, 5-hexenyl or the like, in which the preferred one may be $(C_2-C_4)$alkenyl and the more preferred one may be vinyl, 1-methylvinyl, 2-methylvinyl and 1,3-butadienyl.

Suitable "lower alkynyl" may include straight or branched ones such as ethynyl, 1-propynyl, 1-methylethynyl, 2-butynyl, 2-methyl-3-butynyl, 2-pentynyl, 1-hexynyl or the like, in which the preferred one may be $(C_2-C_4)$alkynyl and the more preferred one may be ethynyl.

Aforesaid "lower aliphatic hydrocarbon group" may have one or more (preferably one to three) suitable substituent(s) such as halogen (e.g., chloro, bromo, fluoro, iodo) or the like.

Suitable "protected amino" may include amino substituted with the conventional amino protective group such as lower alkylamino (e.g., methylamino, ethylamino, propylamino, butylamino, t-butylamino, pentylamino, hexylamino, etc.), di(lower)alkylamino (e.g., dimethylamino, diethylamino, N-ethylpropylamino, dibutylamino, N-(tbutyl)pentylamino, dihexylamino, etc), acylamino explained below or the like.

Suitable "acylamino" may include ureido; lower alkanoylamino (e.g., formylamino, acetylamino, propionylamino, butyrylamino, isobutyrylamino, pivaloylamino, hexanoylamino, etc), lower alkoxycarbonylamino (e.g., methoxycarbonylamino, ethoxycarbonylamino, propoxycarbonylamino, t-butoxycarbonylamino, pentyloxycarbonylamino, hexyloxycarbonylamino, etc), lower alkoxycarbonyl(lower)alkanoylamino (e.g., methoxycarbonylacetylamino, ethoxycarbonylacetylamino, 2-(propoxycarbonyl)propionylamino, 4-(t-butoxycarbonyl)butyrylamino, 2-(butoxycarbonylmethyl)propionylamino, 2-methyl-2-(pentyloxycarbonylmethyl)propionylamino, 6-hexyloxycarbonylhexanoylamino, etc), lower alkanesulfonylamino (e.g., methanesulfonylamino, ethanesulfbnylamino, propanesulfonylamino, butanesulfonylamino, t-butanesulfonylamino, pentanesulfonylamino, hexanesulfonylamino, etc) and the like.

Said "lower alkanoylamino" may have suitable substituent(s) such as di(lower)alkylamino (e.g., dimethylamino, N-methyl-N-ethylamino, dipropylamino, di-t-butylamino, N-pentyl-N-hexylamino, etc); cyclic amino group (e.g., piperidino, etc) which may have lower alkyl; or the like, and suitable examples of said "lower alkanoylamino having suitable substituent(s)" may include lower alkanoylamino having di(lower)alkylamino (e.g., dimethylaminocarbonylamino, 2-dimethylaminoacetylamino, 2-(N-methyl-N-ethylamino) acetylamino, 2-dimethylaminopropionylamino, 3-dipropylaminobutyrylamino, 2-(di-tbutylamino)-2-methylpropionylamino, 2-dimethylaminomethyl-2-methylpropionylamino, 6-(N-pentyl-N-hexylamino) hexanoylamino, etc];

lower alkanoylamino having cyclic amino group which may have lower alkyl [e.g., piperidinocarbonylamino, 2-piperidinoacetylamino, 2-(2-methylpiperidino)-acetylamino, 2-(2-ethylpiperidino)acetylamino, 2-piperidinopropionylamino, 3-(2-ethylpiperidino) butyrylamino, 2-(4-ethylpiperidino-2-methylpropionylamino, 2-piperidinomethyl)-2-methylpropionylamino, 6-(3-propylpiperidino) hexanoylamino, etc]; and the like.

In aforesaid "acylamino", the preferred one may be ureido, (C₁–C₄)alkanoylamino, (C₁–C₄)alkoxycarbonyl-(C₁–C₄)alkanoylamino, di(C₁–C₄)alkylamino(C₁–C₄)alkanoylamino, (C₁–C₄)alkylpiperidino(C₁–C₄)alkanoylamino, (C₁–C₄)alkoxycarbonylamino, (C₁–C₄)alkanesulfonylamino, (C₁–C₄)alkylamino and di(C₁–C₄)alkylamino, in which the more preferred one may be ureido, acetylamino, 2-(ethoxycarbonyl)acetylamino, 2-dimethylaminoacetylamino, 2(2-ethylpiperidino)acetylamino, methoxycarbonylamino, methanesulfonylamino, methylamino and dimethylamino.

Suitable "an acyl group" may include lower alkanoyl (e.g., formyl, acetyl, propionyl, butyryl, isobutyryl, pivaloyl, hexanoyl, etc); other groups are carboxy, protected carboxy, and the like.

Suitable examples of aforesaid "protected carboxy" may be esterified carboxy, in which suitable esterified carboxy may include lower alkoxycarbonyl (e.g., methoxycarbonyl, ethoxycarbonyl, propoxycarbonyl, butoxycarbonyl, t-butoxycarbonyl, pentyloxycarbonyl, hexyloxycarbonyl, etc) which may have N-containing heterocyclic group and the like; amidated carboxy, in which suitable amidated carboxy may include N-(lower)alkylcarbamoyl (e.g., N-methylcarbamoyl, N-ethylcarbamoyl, N-isopropylcarbamoyl, N-butylcarbamoyl, N-pentylcarbamoyl, N-hexylcarbamoyl, etc);

N-(higher)alkylcarbamoyl (e.g. N-heptylcarbamoyl, N-(2-methylheptyl)carbamoyl, N-nonanylcarbamoyl, N-decanylcarbamoyl, N-tricyclo[3.3.1.1³,⁷] decanylcarbamoyl, N-undecanylcarbamoyl, N-(bicyclo [4.3.2]-undecanyl)carbamoyl, N-dodecanylcarbamoyl, N-tridecanylcarbamoyl, N-tetradecanylcarbamoyl, N-pentadecanylcarbamoyl, N-hexadecanylcarbamoyl, N-heptadecanylcarbamoyl, N-octadecanylcarbamoyl, N-nonadecanylcarbamoyl, N-icosanylcarbamoyl, etc);

N,N-di(lower)alkylcarbamoyl [e.g., N,N-dimethylcarbamoyl, N,N-diethylcarbamoyl, N-methyl-N-ethylcarbamoyl, N,N-dipropylcarbamoyl, N,N-di(t-butyl) carbamoyl, N-pentyl-N-hexylcarbamoyl, etc];

N-lower alkyl-N-ar(lower)alkylcarbamoyl (e.g., N-methyl-N-benzylcarbamoyl, etc); a group of the formula:

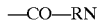

—CO—RN (wherein $R_N$ is N-containing heterocyclic group which may have one or more suitable substituents), in which said group $R_N$ may contain another hetero atom like N, O or S in its ring); or the like.

Suitable "N-containing heterocyclic group" may include saturated or unsaturated, monocyclic or polycyclic heterocyclic group such as unsaturated 3 to 8-membered (more preferably 5 to 7-membered) heteromonocyclic group containing 1 to 4 nitrogen atom(s), for example, azepinyl (e.g., 1H-azepinyl, etc) pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc), tetrazolyl (e.g. 1H-tetrazolyl, 2H-tetrazolyl, etc) etc;

saturated 3 to 8-membered (more preferably 5 to 7 membered) heteromonocyclic group containing 1 to 4 nitrogen atom(s), for example, perhydroazepinyl (e.g. perhydro-1H-azepinyl, etc) pyrrolidinyl, imidazolidinyl, piperidino, piperazinyl, etc;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc;

saturated condensed heterocyclic group containing 1 to 4 nitrogen atom(s), for example, 7-azabicyclo[2.2.1]heptyl, 3-azabicyclo[3.2.2]nonanyl, etc;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc), etc;

saturated 3 to 8-membered (more preferably-5 or 6-membered) heteromonocyclic group containing 1 to 2 oxygen atom(s) and 1 to 3 nitrogen atom(s), for example, morpholinyl, sydnonyl, etc;

unsaturated condensed heterocyclic group containing 1 to 2 oxygen atom(s) and 1 to 3 nitrogen atom(s), for example, benzoxazolyl, benzoxadiazolyl, etc;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc), dihydrothiazinyl, etc;

saturated 3 to 8-membered (more preferably 5 or 6-membered) heteromonocyclic group containing 1 to 2 sulfur atom(s) and 1 to 3 nitrogen atom(s), for example, thiazolidinyl, etc;

unsaturated condensed heterocyclic group containing 1 to 2 sulfur atom(s) and 1 to 3 nitrogen atom(s), for example, benzothiazolyl, benzothiadiazolyl, etc; in which the preferred one may include saturated 3 to 8 membered heteromonocyclic group containing 1 to 4 nitrogen atom(s), saturated condensed heterocyclic group containing 1 to 4 nitrogen atom(s), and saturated 3 to 8 membered heteromonocyclic group containing 1 to 2 oxygen atom(s) and 1 to 3 nitrogen atom(s).

"N-containing heterocyclic group" thus defined may have one or more suitable substituent(s) such as lower alkyl as mentioned above; hydroxy(lower)alkyl (e.g. hydroxymethyl, 1-hydroxyethyl, 2-hydroxyethyl, 3-hydroxypropyl, 2-hydroxybutyl, 1-methyl-1-hydroxymethylethyl, 4-hydroxypentyl, 3-hydroxyhexyl, etc.); (lower alkoxy(lower)alkyl (e.g. methoxymethyl, 2-methoxyethyl, 1-ethoxyethyl, 3-propoxypropyl, 2-(t-butoxy)butyl, 5-pentyloxypentyl, 3-hexyloxyhexyl, etc); acyloxy(lower)alkyl such as lower alkanoyloxy(lower)alkyl (e.g. acetoxymethyl, 1-acetoxyethyl, 2-acetoxyethyl, 2-propionyloxyethyl, 3-propionyloxypropyl, 2-butyryloxybutyl, 4-pivaloyloxypentyl, 6-hexanoyloxyhexyl, etc) or the like; protected carboxy such as lower alkoxycarbonyl as mentioned above; carboxy; acyl(lower)alkyl such as lower alkanoyl(lower)alkyl (e.g. formylmethyl, 1-formylethyl, 2-acetylethyl, 2-formylpropyl, 3-propionylpropyl, 4-formylbutyl, 2-butyrylbutyl, 1-(formylmethyl)ethyl, 3-formylpentyl, 1-isobutyrylpentyl, 4-pivaloylpentyl, 2-formylhexyl, 6-hexanoylhexyl, etc), carboxy(lower)alkyl (e.g. carboxymethyl, 1-carboxyethyl, 2-carboxypropyl, 1-(carboxymethyl)ethyl, 4-carboxybutyl, 3-carboxypentyl, 2-carboxyhexyl, etc), protected carboxy(lower)alkyl, in which the preferred "protected carboxy(lower)alkyl" may be esterified carboxy(lower)alkyl, the most preferred one may be lower alkoxycarbonyl(lower)alkyl (e.g. methoxycarbonylmethyl, 2-methoxycarbonylethyl, 1-ethoxycarbonylethyl, 2-propoxycarbonylpropyl, 1-(methoxycarbonylmethyl)ethyl, 4-t-butoxycarbonylbutyl, 3-pentyloxycarbonylpentyl, 2-hexyloxycarbonylhexyl, etc), amidated carboxy(lower)alkyl, in which the preferred "amidated carboxy(lower)alkyl" may include N-(lower) alkylcarbamoyl(lower)alkyl (e.g. carbamoyl(lower)alkyl, N-ethylcarbamoylmethyl, etc), N,N-di(lower) alkylcarbamoyl(lower)alkyl (e.g., N,N-diethylcarbamoylmethyl, etc.), or the like; or the like.

In aforesaid "N-containing heterocyclic group which may have one or more suitable substituent(s)", the more preferred one may include piperidino which may have 1 to 4 suitable substituent(s) selected from a group consisting of ($C_1$–$C_4$) alkyl, hydroxy($C_1$–$C_4$)alkyl, ($C_1$–$C_4$)alkoxy($C_1$–$C_4$)alkyl, ($C_1$–$C_4$)alkanoyloxy($C_1$–$C_4$)alkyl, ($C_1$$C_4$)alkoxycarbonyl, carboxy, ($C_1$–$C_4$)alkanoyl($C_1$–$C_4$)alkyl, carboxy($C_1$–$C_4$) alkyl, ($C_1$–$C_4$)alkoxycarbonyl($C_1$–$C_4$)alkyl, carbamoyl ($C_1$–$C_4$)alkyl, N-($C_1$–$C_4$)alkylcarbamoyl($C_1$–$C_4$)alkyl, and N,N-di($C_1$–$C_4$)alkylcarbamoyl($C_1$–$C_4$)alkyl (e.g. piperidino, 2-methylpiperidino, 2-ethylpiperidino, 3-ethylpiperidino, 4-ethylpiperidino, 2-propylpiperidino, 4-isopropylpiperidino, 2-butylpiperidino, 3-(t-butyl) piperidino, 2,2,6,6-tetramethylpiperidino, 2,2-dimethyl-6,6-diethylpiperidino, 2-hydroxymethylpiperidino, 3-hydroxymethylpiperidino, 2-(1-hydroxyethyl)piperidino, 2-(2-hydroxyethyl)piperidino, 3-(2-hydroxyethyl) piperidino, 4-(2-hydroxyethyl)piperidino, 2-(3-hydroxypropyl)piperidino, 3-(2-hydroxybutyl)piperidino, 2(1-methyl-1-hydroxymethylethyl)piperidino, 2-methoxymethylpiperidino, 2-(2-methoxyethyl)piperidino, 2-(1-ethoxyethyl)piperidino, 3-(3-propoxypropyl)-piperidino, 4-(2-(t-butoxy)butyl)piperidino, 2-acetoxymethylpiperidino, 3-(1-acetoxyethyl)piperidino, 2-(2-acetoxyethyl)piperidino, 3-(2-propionyloxyethyl) piperidino, 4-(3-propionyloxypropyl)piperidino, 2-(2-butyryloxybutyl)piperidino, 2-methoxycarbonylpiperidino, 2-ethoxycarbonylpiperidino, 2-propoxycarbonylpiperidino, 3-butoxycarbonylpiperidino, 4-(t-butoxycarbonyl) piperidino, 2-carboxypiperidino, 3-carboxypiperidino, 4-carboxypiperidino, 2-(2-hydroxyethyl)-3-methylpiperidino, 2-(2-hydroxyethyl)-4-carboxypiperidino, 2-formylmethylpiperidino, 2-(1-formylethyl)piperidino, 3-(2-acetylethyl)piperidino, 4-(2-formylpropyl)piperidino, 2-(3-propionylpropyl)piperidino, 2-(4-formylbutyl) piperidino, 3-(2-butyrylbutyl)piperidino, 2-[1-(formylmethyl)ethyl]piperidino, 2-carboxymethylpiperidino, 2-(1-carboxyethyl)piperidino, 3-(2-carboxypropyl)piperidino, 4-[1-(carboxymethyl)ethyl] piperidino, 2-(4-carboxybutyl)piperidino, 2-methoxycarbonylmethylpiperidino, 2-(2-methoxycarbonylethyl)piperidino, 3-(2-ethoxycarbonylethyl)piperidino, 4-(2-propoxycarbonylpropyl)piperidino, 2-[1-(methoxycarbonylmethyl)ethyl]piperidino, 2-(4-t-butoxycarbonylbutyl)piperidino, etc);

pyrrolidin-1-yl which may have ($C_1$–$C_4$)alkoxy($C_1$–$C_4$) alkyl (e.g., pyrrolidin-1-yl, 2-methoxymethylpyrrolidin-1-yl, 2-(2-methoxyethyl)pyrrolidin-1-yl, 2-(1-ethoxyethyl) pyrrolidin-1-yl, 3-(3-propoxypropylpyrrolidin-1-yl, 3-{2(t-butoxy)butyl}pyrrolidin-1-yl, etc);

perhydroazepin-1-yl (e.g. perhydro-1H-azepin-1-yl, etc);

piperazin-1-yl which may have ($C_1$–$C_4$)alkyl (e.g. piperazin-1-yl, 2-methylpiperazin-1-yl, 3-methylpiperazin-1-yl, 4-methylpiperazin-1-yl, 2-ethylpiperazin-1-yl, 3-propylpiperazin-1-yl, 4-isopropylpiperazin-1-yl, 2-butylpiperazin-1-yl, 3-(t-butyl)piperazin-1-yl, etc);

morpholino; 7-azabicyclo[2.2.1]heptan-7-yl; 3-azabicyclo[3.2.2]nonan-3-yl; and the like, and the most preferred one may include piperidino, 2-methylpiperidino, 2-ethylpiperidino, 3-ethylpiperidino, 4-ethylpiperidino, 2-propylpiperidino, 2,2,6,6-tetramethylpiperidino, 2-hydroxymethylpiperidino, 2-(2-hydroxyethyl)piperidino, 4-(2-hydroxyethyl)piperidino, 2-methoxymethylpiperidino, 2-(2-methoxyethyl)piperidino, 2-acetoxymethylpiperidino, 2-(2-acetoxyethyl)piperidino, 2-ethoxycarbonylpiperidino, 2-carboxypiperidino, 2-(methoxycarbonylmethyl) piperidino, 2-carboxymethylpiperidino, 2-carbamoylmethylpiperidino, 2-(N-ethylcarbamoylmethyl) piperidino, 2-N,N-diethylcarbamoylmethyl)piperidino, pyrrolidin-1-yl, 2-methoxymethylpyrrolidin-1-yl, perhydro-1H-azepin-1-yl, 4-methylpiperazin-1-yl, morpholino, 7-azabicyclo[2.2.1]heptan-7-yl, 3-azabicyclo[3.2.2]nonan-3-yl, and the like.

Suitable "aryl" may include phenyl, naphthyl, indenyl, anthryl and the like and said "aryl" may have one or more suitable substituent(s) such as halogen (e.g. fluoro, chloro, bromo, iodo), lower alkoxy (e.g. methoxy, ethoxy, propoxy, t-butoxy, pentyloxy, hexyloxy, etc), nitro, amino, protected amino as mentioned before or the like.

The preferred examples of "aryl which may have one or more suitable substituent(s)" may include phenyl which may have 1 to 3 suitable substituent(s) selected from a group consisting of halogen, ($C_1$–$C_4$)alkoxy, nitro, amino, ($C_1$–$C_4$) alkanoylamino, ($C_1$–$C_4$)alkoxycarbonylamino, ($C_1$–$C_4$) alkanesulfonylamino, ($C_1$–$C_4$)alkylamino and di($C_1$–$C_4$) alkylamino, in which the more preferred one may be phenyl, phenyl having chloro, phenyl having methoxy, phenyl having nitro, phenyl having amino, phenyl having acetylamino, phenyl having methoxycarbonylamino, phenyl having methanesulfonylamino, phenyl having methylamino and phenyl having dimethylamino.

Suitable "a heterocyclic group" may include the ones as exemplified for "N-containing heterocyclic group" as mentioned above, unsaturated 3 to 8-membered (more preferably 5 or 6-membered) heteromonocyclic group containing an oxygen atom, for example, furyl, etc;

unsaturated 3 to 8-membered (more preferably 5 or 6-membered) heteromonocyclic group containing an oxygen atom and 1 to 2 sulfur atom(s), for example, dihydrooxathiinyl, etc;

unsaturated condensed heterocyclic group containing 1 to 2 sulfur atom(s), for example, benzothienyl, benzodithiinyl, etc;

unsaturated condensed heterocyclic group containing an oxygen atom and 1 to 2 sulfur atom(s), for example, benzoxathiinyl, etc and the like, in which the preferred one may be unsaturated 3 to 8 membered heteromonocyclic group containing 1 to 4 nitrogen atom(s), the more preferred one may be pyridyl and the most preferred one may be 2-pyridyl, 3-pyridyl and 4-pyridyl.

Suitable "lower alkenyl having halogen" may include 1-fluorovinyl, 1-bromovinyl, 1-chloro-2-methylvinyl, 1-bromo-1-propenyl, 2-chloro-2-propenyl, 1-iodo-1-butenyl, 1-bromo-2-methyl-1-propenyl,, 3-bromo-1,3-butadienyl, 1-chloro-1-pentenyl, 4-chloro-4-pentenyl, 1-bromo-1-hexenyl and the like.

Suitable "lower alkoxy" may include methoxy, ethoxy, propoxy, isopropoxy, butoxy, t-butoxy, pentyloxy, hexyloxy and the like.

Suitable "halogen" may include fluoro, chloro, bromo and iodo.

Suitable "a leaving group" may include di(lower)alkylamino (e.g., dimethylamino, diethylamino, N-ethylpropylamino, dibutylamino, N-pentylhexylamino, etc.), lower alkoxy as mentioned above, halogen as mentioned above, lower alkylthio (e.g. methylthio, ethylthio, propylthio, butylthio, pentylthio, hexylthio, etc.) and the like.

Suitable "unsaturated heterocyclic group" in "unsaturated heterocyclic group which may have one or more suitable substituent(s)" may include unsaturated, monocyclic or polycyclic heterocyclic group containing at least one hetero atom such as nitrogen, oxygen, sulfur or the like.

Suitable examples of said "unsaturated heterocyclic group" may include:

unsaturated 3 to 8-membered (more preferably 5 to 7-membered) heteromonocyclic group containing 1 to 4 nitrogen atom(s), for example, azepinyl (e.g. 1H-azepinyl, etc) pyrrolyl, pyrrolinyl, imidazolyl, pyrazolyl, pyridyl, dihydropyridyl (e.g., 1,2-dihydropyridyl, 1,4-dihydropyridyl, etc), tetrahydropyridyl (e.g., 1,2,3,6-tetrahydropyridyl, etc) pyrimidinyl, dihydropyrimidinyl (e.g. 1,2-dihydropyrimidinyl, etc), pyrazinyl, pyridazinyl, dihydropyridazinyl (e.g., 2,3-dihydropyridazinyl, 1,4-dihydropyridazinyl, etc), tetrahydropyridazinyl (e.g. 2,3,4,5-tetrahydropyridazinyl, etc) triazolyl (e.g., 4H-1,2,4-triazolyl, 1H-1,2,3-triazolyl, 2H-1,2,3-triazolyl, etc), tetrazolyl (e.g., 1H-tetrazolyl, 2H-tetrazolyl, etc), etc;

unsaturated condensed heterocyclic group containing 1 to 4 nitrogen atom(s), for example, indolyl, isoindolyl, indolizinyl, benzimidazolyl, quinolyl, dihydroquinolyl (e.g. 2,3-dihydroquinolyl, etc) isoquinolyl, indazolyl, benzotriazolyl, etc;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, dihydroisoxazolyl (e.g. 2,5-dihydroisoxazolyl, etc) oxadiazolyl (e.g. 1,2,4-oxadiazolyl, 1,3,4-oxadiazolyl, 1,2,5-oxadiazolyl, etc), etc;

unsaturated condensed heterocyclic group containing 1 to 2 oxygen atom(s) and 1 to 3 nitrogen atom(s), for example, benzoxazolyl, benzoxadiazolyl, etc;

unsaturated 3 to 8-membered (more preferably 5 or 6-membered) heteromonocyclic group containing 1 to 2 sulfur atom(s) and 1 to 3 nitrogen atom(s), for example, thiazolyl, dihydrothiazolyl (e.g. 2,3-dihydrothiazolyl, etc) isothiazolyl, thiadiazolyl (e.g. 1,2,3-thiadiazolyl, 1,2,4-thiadiazolyl, 1,3,4-thiadiazolyl, 1,2,5-thiadiazolyl, etc), dihydrothiazinyl, etc;

unsaturated condensed heterocyclic group containing 1 to 2 sulfur atom(s) and 1 to 3 nitrogen atom(s), for example, benzothiazolyl, benzothiadiazolyl, (e.g. benzo[d][1,2,3]thiadiazolyl, etc), imidazothiadiazolyl (e.g. 5H-imidazo[2,1-b][1,3,4]thiadiazolyl, etc), etc;

unsaturated 3 to 8-membered (more preferably 5 or 6-membered) heteromonocyclic group containing 1 to 2 sulfur atom(s), for example, thienyl, dihydrothiinyl, etc;

unsaturated 3 to 8-membered (more preferably 5 or 6-membered) heteromonocyclic group containing an oxygen atom, for example, furyl, etc;

unsaturated 3 to 8-membered (more preferably 5 or 6-membered) heteromonocyclic group containing an oxygen atom and 1 to 2 sulfur atom(s), for example, dihydrooxathiinyl, etc;

unsaturated condensed heterocyclic group containing 1 to 2 sulfur atom(s), for example, benzothienyl, benzodithiinyl, etc;

unsaturated condensed heterocyclic group containing an oxygen atom and 1 to 2 sulfur atom(s) for example, benzoxathiinyl, etc and the like, in which the preferred one may be unsaturated heterocyclic group containing at least one nitrogen atom as hetero atom, the more preferred one may be unsaturated 3 to 8-membered heteromonocyclic group containing 1 to 4 nitrogen atom(s) and unsaturated condensed heterocyclic group containing 1 to 2 sulfur atom(s) and 1 to 3 nitrogen atom(s), the much more preferred one may be pyridazinyl, dihydropyridazinyl, tetrahydropyridazinyl, pyrimidinyl, dihydropyrimidinyl, pyridyl, dihydropyridyl, tetrahydropyridyl, pyrazolyl and imidazothiadiazolyl, and the most preferred one may be pyridazinyl, 2,3-dihydropyridazinyl, 1,4-dihydropyridazinyl, 2,3,4,5-tetrahydropyridazinyl, pyrimidinyl, 1,2-dihydropyrimidinyl, pyridyl, 1,2-dihydropyridyl, 1,4-dihydropyridyl, 1,2,3,6-tetrahydropyridyl, pyrazolyl, and imidazo[2,1-b][1,3,4]thiadiazolyl.

Aforesaid "unsaturated heterocyclic group" may have one or more (preferably 1 to 4) suitable substituent(s) such as lower alkyl (e.g., methyl, ethyl, propyl, isopropyl, butyl, t-butyl, pentyl, hexyl, etc) which may have one or more (preferably 1 to 4) suitable substituent(s) as explained below; carboxy(lower)alkenyl (e.g., 1-carboxyvinyl, 2-carboxyvinyl, 1-carboxy-2-propenyl, 3-carboxy-2-propenyl, 3-carboxy-2-butenyl, 4-carboxy-2-methyl-2-butenyl, 3-carboxy-1-hexenyl, etc); amino; di(lower)alkylamino (e.g. dimethylamino, N-methylethylamino, dipropylamino, N-butyl-(2-methylbutyl)amino, N-pentylhexylamino, etc); halogen (e.g. fluoro, chloro, bromo, iodo, etc); lower alkoxy (e.g., methoxy, ethoxy, propoxy, isopropoxy, butoxy, t-tuboxy, pentyloxy, hexyloxy, etc); oxo; hydroxy; cyano; an acyl group as explained below; or the like.

Suitable "an acyl group" may include lower alkanoyl (e.g., formyl, acetyl, propionyl, butyryl, isobutyryl, pivaloyl, hexanoyl, other groups are), carboxy, protected carboxy, and the like.

Suitable examples of aforesaid "protected carboxy" may be esterified carboxy, in which suitable esterified carboxy may include lower alkoxycarbonyl (e.g., methoxycarbonyl, ethoxycarbonyl, propoxycarbonyl, t-butoxycarbonyl, pentyloxycarbonyl, hexyloxycarbonyl, etc) and the like;

amidated carboxy, in which suitable amidated carboxy may include carbamoyl, N,N-di(lower)alkylcarbamoyl wherein two lower alkyl groups may bond to each other to form 3 to 6-membered ring (e.g., N,N-dimethylcarbamoyl, N-methyl-N-ethylcarbamoyl, N,N-diethylcarbamoyl, N,N-dipropylcarbamoyl, N-butyl-N-t-butylcarbamoyl, N,N-dipentylcarbamoyl, N-pentyl-N-hexylcarbamoyl, 1-aziridinylcarbonyl, 1-azetidinylcarbonyl, 1-pyrrolidinylcarbonyl, piperidinocarbonyl, etc) and the like; or the like.

Suitable examples of "suitable substituent(s)" of aforesaid "lower alkyl which may have one or more suitable substituent(s)" may include hydroxy, aforesaid halogen, aforesaid lower alkoxy, aforesaid an acyl group, and the like.

Suitable examples of said "lower alkyl having one or more suitable substituent(s)" may include lower alkyl having hydroxy and halogen (e.g., 1-hydroxy-1-chloromethyl, 1-hydroxy-2-chloroethyl, 2-hydroxy-3-fluoropropyl, 2-hydroxy-3,3,3-trichloropropyl, 3-bromo-4-hydroxy-4-iodobutyl, 1-chloro-2-hydroxy-4-fluoropentyl, 3,4-dihydroxy-6-chlorohexyl, etc);

hydroxy(lower)alkyl (e.g., hydroxymethyl, 2-hydroxyethyl, 2-hydroxypropyl, 3-hydroxypropyl, 1-hydroxy-1-methylethyl, 1-hydroxybutyl, 1-hydroxymethyl-1-methylethyl, 3-hydroxypentyl, 2-hydroxyhexyl, etc);

lower alkoxy(lower)alkyl (e.g. methoxymethyl, ethoxymethyl, 2-ethoxyethyl, 1-propoxyethyl, 3-isopropoxypropyl, 2-butoxybutyl, 1-t-butoxymethyl-1-methylethyl, 5-pentyloxypentyl, hexyloxymethyl, 3-hexyloxyhexyl, etc);

acyl(lower)alkyl, in which the preferred one may be carboxy(lower)alkyl (e.g. carboxymethyl, 2-carboxyethyl, 2-carboxypropyl, 3-carboxypropyl, 2-carboxy-1-methylethyl, 4-carboxybutyl, 1-carboxymethyl-1-methylethyl, 3-carboxypentyl, 2-carboxyhexyl, etc), and protected carboxy(lower)alkyl, in which the preferred one may be esterified carboxy(lower)alkyl and amidated carboxy(lower)alkyl, the more preferred one may be lower alkoxycarbonyl(lower)alkyl (e.g., methoxycarbonylmethyl, ethoxycarbonylmethyl, 2-methoxycarbonylethyl, 2-ethoxycarbonylethyl, 1-propoxycarbonylethyl, 3-ethoxycarbonylpropyl, 2-butoxycarbonylbutyl, 4-ethoxycarbonylbutyl, 1-t-butoxycarbonylmethyl-1-methylethyl, 5-pentyloxycarbonylpentyl, hexyloxycarbonylmethyl, 3-hexyloxycarbonylhexyl, etc), carbamoyl(lower)alkyl (e.g., carbamoylmethyl, 2-carbamoylethyl, 3-carbamoylpropyl, 2-carbamoyl-1-methylethyl, 4-carbamoylbutyl, 1-carbamoylmethyl-1-methylethyl, 5-carbamoylpentyl, 3-carbamoylhexyl, etc), N,N-di(lower)alkylcarbamoyl(lower)alkyl in which two lower alkyl groups on nitrogen atom may bond to each other to form 3 to 6-membered ring, e.g. N,N-dimethylcarbamoylmethyl, 2-(N,N-dimethylcarbamoyl)-ethyl, 2-(N-methyl-N-ethylcarbamoyl)ethyl, 3-(N-methyl-N-ethylcarbamoyl)propyl, 2-(N,N-dipropylcarbamoyl)-1-methylethyl, 4-(N,N-dipropylcarbamoyl)butyl, 1-(N,N-dimethylcarbamoyl)methyl-1-methylethyl, 5-(N-pentyl-N-hexylcarbamoyl)pentyl, 3-(N-pentyl-N-hexylcarbamoyl) hexyl, (1-aziridinylcarbonyl)methyl, 2-(1-azetidinylcarbonyl)ethyl, 2-(piperidinocarbonyl)ethyl, 3(1-pyrrolidinylcarbonyl)propyl, 2-(piperidinocarbonyl)-1-methylethyl, 4-(1-azetidinylcarbonyl)butyl, 1-(1-aziridinylcarbonyl)methyl-1-methylethyl, 3-(1-pyrrolidinylcarbonyl)pentyl, 6-(piperidinocarbonyl)hexyl, etc]; and the like.

The preferred substituent of "unsaturated heterocyclic group" may be lower alkyl, lower alkyl having hydroxy and halogen, hydroxy(lower)alkyl, lower alkoxy(lower)alkyl, carboxy(lower)alkyl, lower alkoxycarbonyl(lower)alkyl, carbamoyl(lower)alkyl, N,N-di(lower)alkylcarbamoyl (lower)alkyl wherein two lower alkyl groups on nitrogen atom may bond to each other to form 3 to 6-membered ring, carboxy(lower)alkenyl, di(lower)alkylamino, halogen, lower alkoxy, oxo, carboxy, lower alkoxycarbonyl, lower alkanoyl, amino, cyano and hydroxy, in which the more preferred one may be $(C_1–C_4)$alkyl, $(C_1–C_6)$alkyl having hydroxy and halogen, hydroxy$(C_1–C_4)$ alkyl, $(C_1–C_4)$alkoxy$(C_1–C_4)$alkyl, carboxy$(C_1–C_4)$alkyl, $(C_1–C_4)$alkoxycarbonyl$(C_1–C_4)$alkyl, carbamoyl$(C_1–C_4)$ alkyl, N,N-di$(C_1–C_4)$alkylcarbamoyl$(C_1–C_4)$alkyl, piperidinocarbonyl$(C_1–C_4)$alkyl, carboxy$(C_2–C_4)$alkenyl, di$(C_1–C_4)$alkylamino, halogen, $(C_1–C_4)$alkoxy, oxo, carboxy, $(C_1–C_4)$alkoxycarbonyl, $(C_1–C_4)$alkanoyl, amino, cyano and hydroxy, and the most preferred one may be methyl, propyl, 2-hydroxy-3,3,3-trichloropropyl, 2-hydroxyethyl, 3-hydroxypropyl, 2-ethoxyethyl, 2-carboxyethyl, 3-carboxypropyl, 4-carboxybutyl, methoxycarbonylmethyl, 2-methoxycarbonylethyl, 3-ethoxycarbonylpropyl, 4-ethoxycarbonylbutyl, 2-carbamoylethyl, 2-(N,N-dimethylcarbamoyl)ethyl, 2-(piperidinocarbonyl)ethyl, 2-carboxyvinyl, dimethylamino, chloro, methoxy, oxo, carboxy, ethoxycarbonyl, methoxycarbonyl, acetyl, amino, cyano and hydroxy.

Aforesaid "unsaturated heterocyclic group" in "unsaturated heterocyclic group which may have one or more suitable substituent(s)" may have one or more (preferably 1 to 4) substituent(s) explained below as its "one or more suitable substituent(s)" in addition to the ones mentioned above, that is, amino(lower)alkyl; lower alkylamino(lower) alkyl; carboxy(lower)alkylamino(lower)alkyl; protected carboxy(lower)alkylamino(lower)alkyl; lower alkylamino (lower)alkyl having hydroxy and aryloxy, protected amino (lower)alkyl; cyano(lower)alkyl; cyano(higher)alkyl; lower alkyl having heterocyclic group in which heterocyclic group may have one or more suitable substituent(s); higher alkyl having heterocyclic group, in which heterocyclic group may have one or more suitable substituent(s); ar(lower)alkyl; lower alkenyl; or heterocyclic group which may have one or more suitable substituent(s).

Aforesaid substituents are explained in the following.

Suitable "amino(lower)alkyl" may include aminomethyl, 1-aminoethyl, 2-aminoethyl, 2-aminopropyl, 3-aminobutyl, 2-amino-1,1-dimethylethyl, 5-aminopentyl, 1-aminohexyl, and the like, in which the preferred one may be amino $(C_1–C_4)$alkyl and the more preferred one may be 2-aminoethyl.

Suitable "lower alkylamino(lower)alkyl" may include mono- or di- (lower)alkylamino(lower)alkyl" such as methylaminomethyl, 2-(ethylamino)ethyl, 3-(propylamino) propyl, 2-(propylamino)butyl, 2-(tbutylamino)-1,1-dimethylethyl, 4-pentylaminopentyl, 6-hexylaminohexyl, dimethylaminomethyl, 2-dimethylaminoethyl, 1-(N-methylethylamino)ethyl, 1-dimethylaminopropyl, 2-diethylaminopropyl, 3-dimethylaminopropyl, 3-(N-propylbutylamino)butyl, 4-dimethylaminobutyl, 2-dibutylamino-1,1-dimethylethyl, 4-dipentylaminopentyl, 6-(N-pentylhexylamino)hexyl, or the like; and the like, in which the preferred one may be di(lower)alkylamino(lower) alkyl, the more preferred one may be di$(C_1–C_4)$alkylamino $(C_1–C_4)$alkyl and the most preferred one may be 2-dimethylaminoethyl, 3-dimethylaminopropyl and 4-dimethylaminobutyl.

Suitable "carboxy(lower)alkylamino(lower)alkyl" may include carboxymethylaminomethyl, 2-(carboxymethylamino)ethyl, 2-(1-carboxyethylamino) ethyl, 3-(2-carboxypropylamino)propyl, 2-(3-carboxypropylamino)butyl, 2-(2-carboxy-1,1-dimethylethylamino)-1,1-dimethylethyl, 4-(5-carboxypentylamino)pentyl, 6-(3-carboxyhexylamino) hexyl, and the like, in which the preferred one may be carboxy($C_1$–$C_4$)alkylamino($C_1$–$C_4$)alkyl and the most preferred one may be 2-(carboxymethylamino)ethyl.

Suitable "protected carboxy" in "protected carboxy (lower)alkylamino(lower)alkyl" may be an esterified carboxy group, or the like, and concrete examples of the ester moiety in said esterified carboxy group may be the ones such as lower alkyl ester e.g., methyl ester, ethyl ester, propyl ester, isopropyl ester, butyl ester, isobutyl ester, tert-butyl ester, pentyl ester, hexyl ester, 1-cyclopropylethyl ester, etc which may have suitable substituent(s), for example, lower alkanoyloxy(lower)alkyl ester e.g., acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc], lower alkanesulfonyl(lower)alkyl ester, e.g., 2-mesylethyl ester, etc or mono(or di or tri)halo(lower)alkyl ester e.g. 2-iodoethyl ester, 2,2,2-trichloroethyl ester, etc; lower alkenyl ester e.g., vinyl ester, allyl ester, etc; lower alkynyl ester e.g., ethynyl ester, propynyl ester, etc; ar(lower)alkyl ester which may have suitable substituent(s), e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tertbutylbenzyl ester, etc; aryl ester which may have suitable substituent(s) e.g. phenyl ester, 4-chlorophenyl ester, tolyl ester, 4-tert-butylphenyl ester, xylyl ester, mesityl ester, cumenyl ester, etc]; or the like.

Suitable example of "protected carboxy(lower) alkylamino(lower)alkyl" may be esterified carboxy(lower) alkylamino(lower)alkyl, in which the preferred one may be lower alkoxycarbonyl(lower)alkylamino(lower)alkyl such as methoxycarbonylmethylaminomethyl, 2-(ethoxycarbonylmethylamino)ethyl, 2-(1-ethoxycarbonylethylamino)ethyl, 3-(2-propoxycarbonylpropylamino)propyl, 2-(3-butoxycarbonylpropylamino)butyl, 2-(2-t-butoxycarbonyl-1,1-dimethylethylamino)-1,1-dimethylethyl, 4-(5-pentyloxycarbonylpentylamino)pentyl, 6-(3-hexyloxycarbonylhexylamino)hexyl, or the like; the more preferred one may be ($C_1$–$C_4$)alkoxycarbonyl-($C_1$–$C_4$) alkylamino($C_1$–$C_4$)alkyl, and the most preferred one may be 2-(ethoxycarbonylmethylamino)ethyl.

Suitable "lower alkylamino(lower)alkyl having hydroxy and aryloxy" may be aforesaid "lower alkylamino(lower) alkyl" having "hydroxy" and "aryloxy" (e.g., phenoxy, tolyloxy, naphthyloxy, etc) and suitable examples thereof may include 1-(1-naphthyloxy)-1-hydroxymethylaminomethyl 2-(1-hydroxy-2-phenoxyethylamino)ethyl 2-[2-hydroxy-3-(1-naphthyloxy) propylamino]ethyl 2-[4-hydroxy-3-(p-tolyloxy)butylamino] propyl, 2-[4-hydroxy-1-(2-naphthyloxy)butylamino]-1,1-dimethylethyl, 4-[1-hydroxy-5-(1-naphthyloxy) pentylamino]pentyl, 6-[2-hydroxy-4-(2-naphthyloxy) hexylamino]hexyl, in which the preferred one may be ($C_1$–$C_4$)alkylamino($C_1$–$C_4$)alkyl having hydroxy and naphthyloxy and the more preferred one may be 2-[2-hydroxy-3-(1-naphthyloxy)propylamino]ethyl.

Suitable "protected amino(lower)alkyl" may be acylamino(lower)alkyl.

Suitable example of the acylamino may be lower alkanoylamino e.g., formylamino, acetylamino, propionylamino, hexanoylamino, pivaloylamino, mono(or di or tri)halo (lower)alkanoylamino e.g., chloroacetylamino, trifluoroacetylamino, lower alkoxycarbonylamino e.g., methoxycarbonylamino, ethoxycarbonylamino, tert-butoxycarbonylamino, tert-pentyloxycarbonylamino, hexyloxycarbonylamino, mono(or di or tri)halo(lower) alkoxycarbonylamino e.g., chloromethoxycarbonylamino, dichloroethoxycarbonylamino, trichloroethoxycarbonylamino, aroylamino e.g., benzoylamino, toluoylamino, xyloylamino, naphthoylamino, ar(lower)alkanoylamino such as phenyl (lower)alkanoylamino e.g., phenylacetylamino, phenylpropionylamino, aryloxycarbonylamino [e.g. phenoxycarbonylamino, naphthyloxycarbonylamino, etc], aryloxy(lower)alkanoylamino such as phenoxy(lower) alkanoylamino e.g., phenoxyacetylamino, phenoxypropionylamino, arylglyoxyloylamino e.g., phenylglyoxyloylamino, naphthylglyoxyloylamino, ar(lower)alkoxycarbonylamino which may have suitable substituent(s) such as phenyl(lower)alkoxycarbonylamino which may have nitro or lower alkoxy, e.g., benzyloxycarbonylamino, phenethyloxycarbonylamino, p-nitrobenzyloxycarbonylamino, p-methoxybenzyloxycarbonylamino, thienylacetylamino, imidazolylacetylamino, furylacetylamino, tetrazolylacetylamino, thiazolylacetylamino, thiadiazolylacetylamino, thienylpropionylamino, thiadiazolylpropionylamino, lower alkylsulfonylamino e.g., methylsulfonylamino, ethylsulfonylamino, propylsulfonylamino, isopropylsulfonylamino, pentylsulfonylamino, butylsulfonylamino, etc, arylsulfonylamino e.g., phenylsulfonylamino, tolylsulfonylamino, xylylsulfonylamino, naphthylsulfonylamino, etc, ar(lower) alkylsulfonylamino such as phenyl(lower) alkylsulfonylamino e.g., benzylsulfonylamino, phenethylsulfonylamino, benzhydrylsulfonylamino, etc, imido e.g., 1,2-cyclohexanedicarboximido, succinimido, phthalimido, etc, and the like.

Preferred example of said "protected amino(lower)alkyl" may be imido(lower)alkyl such as phthalimidomethyl, 2-phthalimidoethyl, 1-(1,2-cyclohexanedicarboximido) ethyl, 2-succinimidopropyl, 3-phthalimidobutyl, 2-(1,2-cyclohexanedicarboximido)-1,1-dimethylethyl, 5-phthalimidopentyl, 1-phthalimidohexyl, or the like, the more preferred one may be imido($C_1$–$C_4$)alkyl and the most preferred one may be 2-phthalimidoethyl.

Suitable "cyano(lower)alkyl" may include cyanomethyl, 1-cyanoethyl, 2-cyanoethyl, 3-cyanopropyl, 2-cyanobutyl, 4-cyanobutyl, 2-cyano-1,1-dimethylethyl, 4-cyanopentyl, 5-cyanopentyl, 6-cyanohexyl and the like, in which the preferred one may be cyano($C_1$–$C_6$)alkyl and the most preferred one may be cyanomethyl, 2-cyanoethyl, 3-cyanopropyl, 4-cyanobutyl, 5-cyanopentyl and 6-cyanohexyl.

Suitable "cyano(higher)alkyl" may include 7-cyanoheptyl, 8-cyanooctyl, 4-cyanooctyl, 8-cyano-3-methylheptyl, 9-cyanononyl, 1-cyanononyl, 10-cyanodecyl, 8-cyanoundecyl, 12-cyanododecyl, 11-cyano-4-methylundecyl, 13-cyanotridecyl, 6-cyanotetradecyl, 15-cyanopentadecyl, 12-cyanohexadecyl, 17-cyanoheptadecyl, 4-cyanooctadecyl, 19-cyanononadecyl, 1-cyano-12-ethylheptadecyl, 20-cyanoicosyl, and the like, in which the preferred one may be cyano($C_7$–$C_{16}$)alkyl and the more preferred one may be 7-cyanoheptyl, 8-cyanooctyl, 9-cyanononyl, 10-cyanodecyl and 12-cyanododecyl.

Suitable "lower alkyl" may be a straight or branched one such as methyl, ethyl, propyl, isopropyl, butyl, t-butyl, pentyl, hexyl or the like.

Suitable "lower alkenyl" may be a straight or branched one such as vinyl, allyl, 2-butenyl, 2-methyl-2-propenyl, 4-pentenyl, 3-hexenyl, or the like, in which the preferred one may be $(C_2-C_4)$alkenyl and the more preferred one may be vinyl.

Suitable "lower alkyl" in "lower alkyl having heterocyclic group, in which heterocyclic group may have one or more suitable substituent(s)" can be referred to the ones as exemplified before, and the preferred one may be $(C_1-C_6)$alkyl and the most preferred one may be methyl, ethyl, propyl, butyl, pentyl and hexyl.

Suitable "higher alkyl" in "higher alkyl having heterocyclic group, in which heterocyclic group may have one or more suitable substituent(s)" may include heptyl, octyl, 3-methylheptyl, nonyl, 2,6-dimethylheptyl, decyl, undecyl, dodecyl, 4-methyldodecyl, tridecyl, tetradecyl, pentadecyl, hexadecyl, heptadecyl, octadecyl, nonadecyl, 12-ethylheptadecyl, icosyl and the like, in which the preferred one may be $(C_7-C_{16})$alkyl, and the more preferred one may be heptyl, octyl, nonyl, decyl, and dodecyl.

Suitable "heterocyclic group" in "lower alkyl having heterocyclic group, in which heterocyclic group may have one or more suitable substituent(s)" and "higher alkyl having heterocyclic group, in which heterocyclic group may have one or more suitable substituent(s)" means saturated or unsaturated, monocyclic or polycyclic heterocyclic group containing at least one hetero-atom such as an oxygen, sulfur, nitrogen atom and the like. And, especially preferable heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc), tetrazolyl (e.g., 1H-tetrazolyl, 2H-tetrazolyl, etc), dihydrotriazinyl (e.g., 4,5-dihydro-1,2,4-triazinyl, 2,5-dihydro-1,2,4-triazinyl, etc), etc; saturated 3 to 8-membered heteromonocyclic group containing 1 to 4 nitrogen atom(s), for example, pyrrolidinyl, imidazolidinyl, piperidyl (e.g., piperidino, etc), piperazinyl, etc; unsaturated condensed heterocyclic group containing 1 to 5 nitrogen atom(s), for example, indolyl, isoindolyl, indolizinyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc), dihydrotriazolopyridazinyl, etc; unsaturated 3 to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc), etc; saturated 3 to 8-membered heteromonocyclic group containing 1 to 2 oxygen atom(s) and 1 to 3 nitrogen atom(s), for example, morpholinyl, oxazolidinyl (e.g., 1,3-oxazolidinyl, etc), etc; unsaturated condensed heterocyclic group containing 1 to 2 oxygen atom(s) and 1 to 3 nitrogen atom(s), for example, benzoxazolyl, benzoxadiazolyl, etc; unsaturated 3 to 8-membered heteromonocyclic group containing 1 to 2 sulfur atom(s) and 1 to 3 nitrogen atom(s), for example, 1,3-thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc; saturated 3 to 8-membered heteromonocyclic group containing 1 to 2 sulfur atom(s) and 1 to 3 nitrogen atom(s), for example, thiazolidinyl, etc; unsaturated 3 to 8-membered heteromonocyclic group containing a sulfur atom, for example, thienyl, etc; unsaturated condensed heterocyclic group containing 1 to 2 sulfur atom(s) and 1 to 3 nitrogen atom(s), for example, benzothiazolyl, benzothiadiazolyl, etc; unsaturated 3 to 8-membered heteromonocyclic group containing 1 to 2 oxygen atom(s), for example, furyl, pyranyl, dioxolyl, etc; saturated 3 to 8-membered heteromonocyclic group containing 1 to 2 oxygen atom(s), for example, oxolanyl, tetrahydropyranyl (e.g. tetrahydro-2H-pyran-2-yl, etc), dioxolanyl, etc; unsaturated condensed heterocyclic group containing 1 to 2 oxygen atom(s), for example, isobenzofuranyl, chromenyl (e.g., 2H-chromen-3-yl, etc), dihydrochromenyl (e.g. 3,4-dihydro-2H-chromen-4-yl, etc), etc; and the like.

Preferred example of aforesaid "heterocyclic group" may be unsaturated 3 to 8-membered heteromonocyclic group containing 1 to 4 nitrogen atom(s); saturated 3 to 8-membered heteromonocyclic group containing 1 to 4 nitrogen atom(s); saturated 3 to 8-membered heteromonocyclic group containing 1 to 2 oxygen atom(s) and 1 to 3 nitrogen atom(s); and saturated 3 to 8-membered heteromonocyclic group containing 1 to 2 oxygen atom(s); in which the preferred one may be pyridyl, tetrazolyl, piperidyl, piperazinyl, morpholinyl, oxazolidinyl and tetrahydropyranyl; and the more preferred one may be 4-pyridyl, 1H-tetrazol-5-yl, piperidino, 1-piperazinyl, morpholino, 1,3-oxazolidin-5-yl and tetrahydro-2H-pyran-2-yl.

"heterocyclic group" thus explained may have one or more (preferably 1 to 3) suitable substituent(s) such as hydroxy(lower)alkyl (e.g. hydroxymethyl, 2-hydroxyethyl, 1-hydroxypropyl, 4-hydroxybutyl, 2-hydroxy-1,1-dimethylethyl, 3-hydroxypentyl, 6-hydroxyhexyl, etc), aryl which may have lower alkoxy (e.g., phenyl, naphthyl, 2-methoxyphenyl, 2-methoxynaphthyl, 3-ethoxyphenyl, 4-propoxyphenyl, 2-butoxyphenyl, 5-propoxynaphthyl, 3-t-butoxyphenyl, 4-pentyloxyphenyl, 2-hexyloxyphenyl, etc), oxo, or the like, in which preferred "suitable substituent(s)" may be hydroxy$(C_1-C_4)$alkyl, phenyl having $(C_1-C_4)$alkoxy and oxo, and the more preferred one may be 2-hydroxyethyl, 2-methoxyphenyl and oxo.

Suitable "heterocyclic group" in "heterocyclic group which may have one or more suitable substituent(s)" can be referred to the ones exemplified for "heterocyclic group" of "lower alkyl having heterocyclic group, in which heterocyclic group may have one or more suitable substituent(s)" and "higher alkyl having heterocyclic group, in which heterocyclic group may have one or more suitable substituent(s)", and the preferred one may be an unsaturated condensed heterocyclic group containing 1 to 2 oxygen atom(s), the more preferred one may be dihydrochromenyl, and the most preferred one may be 3,4-dihydro-2H-chromen-4-yl.

This "heterocyclic group" may have one or more (preferably 1 to 4) suitable substituent(s) such as aforesaid lower alkyl, hydroxy, cyano or the like, in which the preferred one may be $(C_1-C_4)$alkyl, hydroxy and cyano, and the most preferred one may be methyl, hydroxy and cyano.

Suitable "ar(lower)alkyl" may include mono- or di- or triphenyl(lower)alkyl (e.g. benzyl, phenethyl, 2-phenylpropyl, 4-phenylbutyl, 2-phenyl-1,1-dimethylethyl, 1-phenylpentyl, 6-phenylhexyl, benzhydryl, trityl, etc) and the like, in which the preferred one may be phenyl$(C_1-C_4)$alkyl and the most preferred one may be benzyl.

Suitable "N-containing heterocyclic group" in "N-containing heterocyclic group which may have one or more suitable substituent(s)" may be heterocyclic group having at least one nitrogen atom as its ring member among the aforesaid "heterocyclic group", and said "N-containing heterocyclic group" may have one or more (preferably 1 to 3) suitable substituent(s) such as aforesaid hydroxy(lower) alkyl, aforesaid aryl which may have lower alkoxy, oxo or the like.

Suitable "tetrazolyl(lower)alkyl" may be 1H-tetrazol-5-ylmethyl, 2-(1H-tetrazol-5-yl)ethyl, 3-(1H-tetrazol-5-yl)propyl, 4-(1H-tetrazol-5-yl)butyl, 2-(2H-tetrazol-2-yl)-1,1-dimethylethyl, 4-(1H-tetrazol-1-yl)pentyl, 5-(1H-tetrazol-5-yl)pentyl, 6-(1H-tetrazol-5-yl)hexyl, or the like, in which the preferred one may be tetrazolyl($C_1$–$C_6$)alkyl and the more preferred one may be (1H-tetrazol-5-yl)methyl, 2-(1H-tetrazol-5-yl)ethyl, 3-(1H-tetrazol-5-yl)propyl, 4-(1H-tetrazol-5-yl)butyl, 5-(1H-tetrazol-5-yl)pentyl and 6-(1H-tetrazol-5-yl)hexyl.

Suitable "tetrazolyl(higher)alkyl" may be 7-(1H-tetrazol-5-yl)heptyl, 8-(1H-tetrazol-5-yl)octyl, 4-(1H-tetrazol-1-yl)octyl, 8-(1H-tetrazol-5-yl)-3-methylheptyl, 9-(1H-tetrazol-5-yl)nonyl, 1-(1H-tetrazol-1-yl)nonyl, 10-(1H-tetrazol-5-yl)decyl, 8-(1H-tetrazol-5-yl)undecyl, 12-(1H-tetrazol-5-yl)dodecyl, 11-(1H-tetrazol-5-yl)-4-methylundecyl, 13-(1H-tetrazol-5-yl)tridecyl, 6(1H-tetrazol-5-yl)tetradecyl, 15-(1H-tetrazol-5-yl)pentadecyl, 12-(1H-tetrazol-5-yl) hexadecyl, 17-(1H-tetrazol-1-yl)heptadecyl, 4-(1H-tetrazol-5-yl)- octadecyl, 19-(1H-tetrazol-5-yl)nonadecyl, 1-(1H-tetrazol-1-yl)-12-ethylheptadecyl, 20-(1H-tetrazol-5-yl)icosyl, or the like, in which the preferred one may be tetrazolyl($C_7$–$C_{16}$)alkyl and the more preferred one may be 7-(1H-tetrazol-5-yl)heptyl, 8-(1H-tetrazol-5-yl)octyl, 9-(1H-tetrazol-5-yl)nonyl, 10-(1H-tetrazol-5-yl)decyl and 12-(1H-tetrazol-5-yl)dodecyl.

In the pyrazolopyridine compound (I) thus explained, the especially preferred compound for working the present invention may include the following ones.

(1) (2R)-1-[3-(2-Phenylpyrazolo[1,5-a]pyridin-3-yl) acryloyl]-2-(2-hydroxyethyl)piperidine (trans isomer)

(2) 3-[2-(3-Carboxypropyl)-3-oxo-2,3-dihydropyridazin-6-yl]-2-phenylpyrazolo[1,5-a]pyridine (3) (2R)-1-[3-(2-Phenylpyrazolo[1,5-a]pyridin-3-yl) acryloyl]-2-(carboxymethyl)piperidine (trans isomer) The pharmaceutical composition of the present invention can be used in the form of the pyrazolopyridine compound (I) alone, as an active ingredient, or in the form of a pharmaceutical preparation, for example, in solid, semisolid or liquid form, which contains the pyrazolopyridine compound (I) or a salt thereof, as an active ingredient in admixture with an organic or inorganic carrier or excipient suitable for rectal, pulmonary (nasal or buccal inhalation), ocular, or oral or parenteral (including subcutaneous, intravenous and intramuscular) administrations.

The active ingredient may be compounded, for example, with the usual non-toxic, pharmaceutically acceptable carriers for tablets, pellets, troches, capsules, suppositories, aerosols, powders for insufflation, solutions, emulsions, suspensions, and any other form suitable for use. And, if necessary, in addition, auxiliary, stabilizing, thickening and coloring agents and perfumes may be used.

The pyrazolopyridine compound (I) or a salt thereof is/are included in the pharmaceutical composition in an amount sufficient to produce the desired preventive and/or treating effect upon the process or condition of the diseases.

The pharmaceutical composition of the present invention can be manufactured by the conventional method in this field of the art. If necessary, the technique generally used in this field of the art for improving the bioavailability of a drug can be applied to the pharmaceutical composition of the present invention.

For applying the composition, it is preferable to apply it by intravenous including i.v. infusion, intramuscular, or oral administration.

While the dosage of therapeutically effective amount of the pyrazolopyridine compound (I) varies from and also depends upon the age and condition of each individual patient to be treated, in the case of intravenous administration, a daily dose of 0.01–100 mg of the pyrazolopyridine compound (I) per kg weight, in the case of intramuscular administration, a daily dose of 0.01–100 mg of the pyrazolopyridine compound (I) per kg weight, in case of oral administration, a daily dose of 0.01–200 mg of the pyrazolopyridine compound (I) per kg weight is generally given.

What is claimed is:

1. A method of preventing or treating dialysis-induced hypotension and/or hypotension subsequent to dialysis, comprising:

administering to a subject a therapeutically effective amount of a pyrazolopyridine compound represented by the formula (I):

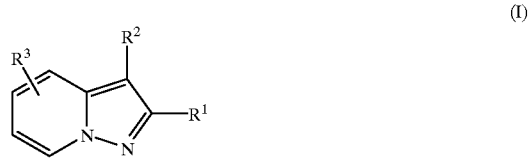

wherein $R^1$ is (1) lower alkyl, (2) aryl, (3) aryl substituted by at least one substituent selected from the group consisting of halogen, lower alkoxy, nitro, amino and protected amino, (4) an unsaturated heterocyclic group selected from the group consisting of pyrrolyl, pyrrolinyl, imidazolyl, pyridyl, pyridyl N-oxide, dihydropyridyl, tetrahydropyridyl, pyridazinyl, furyl, and thienyl, (5) an unsaturated heterocyclic group selected from the group consisting of pyrrolyl, pyrrolinyl, imidazolyl, pyridyl, pyridyl N-oxide, dihydropyridyl, tetrahydropyridyl, pyridazinyl, furyl, and thienyl, which is substituted with at least one substituent selected from the group consisting of lower alkyl, hydroxy(lower)alkyl, (lower)alkoxy(lower)alkyl, acyloxy(lower)alkyl, lower alkoxycarbonyl, carboxy, acyl(lower)alkyl, carboxy(1ower)alkyl, protected carboxy(lower)alkyl;

(6) a saturated heterocyclic group selected from the group consisting of pyrrolidinyl and piperidino, or (7) an saturated heterocyclic group selected from the group consisting of pyrrolidinyl and piperidino, which is substituted with at least one substituent selected from the group consisting of lower alkyl, hydroxy(lower)alkyl, (lower)alkoxy(lower)alkyl, acyloxy(lower)alkyl, lower alkoxycarbonyl, carboxy, acyl(lower)alkyl, carboxy(lower)alkyl, protected carboxy(lower)alkyl, carboxy(lower)alkenyl, amino, di(lower)alkylamino, lower alkoxy, oxo, hydroxy, cyano, acyl, carboxy or protected carboxy;

R² is (1) a group of the formula:

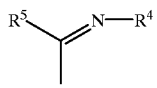

wherein R⁴ is protected amino or hydroxy and R⁵ is hydrogen or lower alkyl, (2) cyano, or (3) a group of the formula:

wherein R⁶ is an acyl group, carboxy or protected carboxy, and A is a lower aliphatic hydrocarbon group optionally substituted with at least one substituent selected from the group consisting of hydroxy, halogen, lower alkoxy and acyl, (4) amidated carboxy, (5) an unsaturated heterocyclic group selected from the group consisting of pyrrolyl, pyrrolinyl, imidazolyl, pyridyl, pyridyl N-oxide, dihydropyridyl, tetrahydropyridyl, pyridazinyl, dihydropyridazinyl, tetrahydropyridazinyl, pyrimidyl, dihydropyrimidinyl, pyrazolyl, imidazothiadiazolyl, furyl, and thienyl, optionally substituted with at least one substituent selected from the group consisting of lower alkyl, caboxy(lower)alkyl, carboxy(lower)alkenyl, amino, di(lower)alkylamino, halogen, lower alkoxy, oxo, hydroxy, cyano and acyl, (6) amino, or (7) protected amino; and R³ is hydrogen, lower alkyl, lower alkoxy or halogen;

or a salt thereof.

2. The method of claim 1, wherein said unsaturated heterocyclic group in (5) of the definition of R² is selected from the group consisting of pyrrolyl, pyrrolinyl, imidazolyl, pyridyl, pyridyl N-oxide, dihydropyridyl, tetrahydropyridyl, pyridazinyl, furyl, and thienyl.

3. The method of claim 1, wherein R¹ is lower alkyl.

4. The method of claim 1, wherein R¹ is aryl.

5. The method of claim 1, wherein R¹ is aryl substituted by at least one substituent.

6. The method of claim 1, wherein R¹ is said heterocyclic group.

7. The method of claim 1, wherein R² is (1).

8. The method of claim 1, wherein R² is (2).

9. The method of claim 1, wherein R² is (3).

10. The method of claim 1, wherein R² is (4).

11. The method of claim 1, wherein R² is (5).

12. The method of claim 1, wherein R² is (6).

13. The method of claim 1, wherein R² is (7).

14. The method of claim 1, wherein R² is (5) and said carboxy(lower)alkyl in (5) is selected from the group consisting of carboxymethyl, 2-carboxyethyl, 2-carboxypropyl, 3-carboxypropyl, 2-carboxy-1-methylethyl, 4-carboxybutyl, 1-carboxymethyl-1-methylethyl, 3-carboxypentyl and 2-carboxyhexyl.

15. The method of claim 1, wherein R² is (5) and said unsaturated heterocyclic group is substituted with at least one of said carboxy(lower)alkyl substituent.

16. The method of claim 1, wherein said said carboxy (lower)alkyl substituent is selected from the group consisting of carboxymethyl, 2-carboxyethyl, 2-carboxypropyl, 3-carboxypropyl, 2-carboxy-1-methylethyl, 4-carboxybutyl, 1-carboxymethyl-1-methylethyl, 3-carboxypentyl and 2-carboxyhexyl.

17. The method of claim 1, wherein

R¹ is aryl, and

R² is (5) and said unsaturated heterocyclic group is substituted with at least one carboxy(lower)alkyl.

18. The method of claim 17, wherein R¹ is phenyl, and R² is dihydropyridazinyl substituted with at least one carboxy (lower)alkyl.

19. The method of claim 18, wherein the compound represented by formula (I) is 3-[2-(3-carboxypropyl)-3-oxo-2,3-dihydropyridazin-6-yl]-2-phenylpyrazolo[1,5-a] pyridine.

20. A method of preventing or treating dialysis-induced hypotension and/or hypotension subsequent to dialysis, comprising:

administering to a subject a therapeutically effective amount of a pyrazolopyridine compound is represented by the formula:

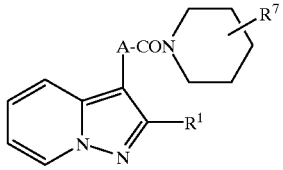

wherein

R¹ is aryl,

R⁷ is acyl(lower)alkyl, and

A is lower alkenyl.

21. The method of claim 20, wherein R¹ is phenyl and R⁷ is carboxy(lower)alkyl.

22. The method of claim 20, wherein the pyrazolopyridine compound is 1-[3-(2-phenylpyrazolo[1,5-a]pyridin-3-yl) acryloyl]-2-(carboxy methyl)piperidine.

* * * * *